(12) United States Patent
Onoe et al.

(10) Patent No.: US 8,591,426 B2
(45) Date of Patent: Nov. 26, 2013

(54) SELF-LUMINOUS SENSOR DEVICE

(75) Inventors: Atsushi Onoe, Saitama (JP); Yoshinori Kimura, Hanno (JP)

(73) Assignee: Pioneer Corporation, Kanagawa (JP)

( * ) Notice: Subject to any disclaimer, the term of this patent is extended or adjusted under 35 U.S.C. 154(b) by 461 days.

(21) Appl. No.: 12/991,965

(22) PCT Filed: May 12, 2008

(86) PCT No.: PCT/JP2008/058693
§ 371 (c)(1),
(2), (4) Date: Dec. 3, 2010

(87) PCT Pub. No.: WO2009/139028
PCT Pub. Date: Nov. 19, 2009

(65) Prior Publication Data
US 2011/0092832 A1    Apr. 21, 2011

(51) Int. Cl.
*A61B 5/02* (2006.01)
*A61B 5/00* (2006.01)

(52) U.S. Cl.
USPC ............................. 600/504; 600/323; 600/479

(58) Field of Classification Search
USPC ........................................................ 600/504
See application file for complete search history.

(56) References Cited

U.S. PATENT DOCUMENTS

| | | | |
|---|---|---|---|
| 5,109,849 A | 5/1992 | Goodman et al. | |
| 5,797,841 A * | 8/1998 | Delonzor et al. | 600/323 |
| 6,256,523 B1 * | 7/2001 | Diab et al. | 600/323 |
| 2003/0147140 A1 | 8/2003 | Ito | |
| 2006/0209416 A1 | 9/2006 | Kim et al. | |
| 2008/0097172 A1 | 4/2008 | Sawada | |

FOREIGN PATENT DOCUMENTS

| | | |
|---|---|---|
| EP | 1810613 | 7/2007 |
| JP | 2001-198111 | 7/2001 |
| JP | 2004-229920 | 8/2004 |
| JP | 2004-357784 | 12/2004 |
| JP | 2005-31379 | 2/2005 |
| JP | 2006-130208 | 5/2006 |
| WO | 96/13208 | 5/1996 |
| WO | WO 2007/097240 | 8/2007 |

OTHER PUBLICATIONS

Supplementary European Search Report dated Jul. 8, 2011 in corresponding European Application No. 08 75 2576.
International Search Report, PCT/JP2008/058693, Jun. 10, 2008.

* cited by examiner

*Primary Examiner* — Navin Natnithithadha
*Assistant Examiner* — Michael R Bloch
(74) *Attorney, Agent, or Firm* — Young & Thompson

(57) ABSTRACT

A light-emitting sensor device is provided with a substrate (110); an irradiating part (120), disposed on the substrate, for applying light to a specimen; a light receiving part (150), disposed on the substrate, for detecting light from the specimen caused by the applied light; a light scattering part, disposed at least one of between the irradiating part and the specimen and between the specimen and the light receiving part, for scattering at least one of light emitted from the irradiating part and the light from the specimen. The sensor device stably detects a predetermined type of information, such as a blood flow velocity, on the specimen.

9 Claims, 17 Drawing Sheets

Comparative example: if there is no scatterer

Comparative example: if there is no scatterer

SELF-LUMINOUS SENSOR DEVICE

TECHNICAL FIELD

The present invention relates to a light-emitting sensor device capable of measuring a blood flow velocity or the like.

BACKGROUND ART

As this type of light-emitting sensor device, there is a device for applying light such as laser light to a living body and for calculating the blood flow velocity of the living body from a change in wavelength by Doppler shift in its reflection or scattering (e.g. refer to patent documents 1 to 3).

On the other hand, for example, in a patent document 4, there is suggested a technology in which measurement accuracy is increased by providing a light scatterer on light incoming side and outgoing side with respect to body tissue on a device for measuring the concentration of a light absorbing material in the body tissue by using a pulse photometry technology.

Patent document 1: Japanese Patent Application Laid Open No. 2004-357784
Patent document 2: Japanese Patent Application Laid Open No. 2004-229920
Patent document 3: Japanese Patent Application Laid Open No. 2006-130208
Patent document 4: Japanese Patent Application Laid Open No. 2001-198111

DISCLOSURE OF INVENTION

Subject to be Solved by the Invention

However, according to the aforementioned light-emitting sensor device, there is a technical problem in which the detection value, such as a blood flow velocity, of the living body likely varies due to the subtle movement of the living body and a change in pressure on the living body in detection. Thus, if the aforementioned light-emitting sensor device is used as a medical device, there is a possibility that the accuracy of the detection value, such as a blood flow velocity, of the living body is not sufficiently reliable.

In view of the aforementioned problems, it is therefore an object of the present invention to provide a light-emitting sensor device which reduces a change in the detection value due to a shift in relative position relation between the light-emitting sensor device and a specimen and which can stably detect a predetermined type of information, such as a blood flow velocity, on the specimen.

Means for Solving the Subject

The above object of the present invention can be achieved by a light-emitting sensor device provided with: a substrate; an irradiating part, disposed on the substrate, for applying light to a specimen; a light receiving part, disposed on the substrate, for detecting light from the specimen caused by the applied light; a light scattering part, disposed at least one of between the irradiating part and the specimen and between the specimen and the light receiving part, for scattering at least one of light emitted from the irradiating part and the light from the specimen.

According to the light-emitting sensor device of the present invention, in its detection, the light such as laser light is applied to the specimen, which is one portion of a living body, by the irradiating part including e.g. a semiconductor laser. The light from the specimen caused by the light applied to the specimen in this manner is detected by the light receiving part including e.g. a light receiving element. Here, the "light from the specimen caused by the light applied to the specimen" means light caused by the light applied to the specimen, such as lights reflected, scattered, diffracted, refracted, transmitted through, Doppler-shifted in the specimen and interfering light by the above lights. On the basis of the light detected by the light receiving part, it is possible to obtain predetermined information such as a blood flow velocity associated with the specimen.

In the present invention, in particular, the light scattering part is disposed at least one of between the irradiating part and the specimen and between the specimen and the light receiving part. The light scattering part is made of a fibrous material such as a woven fabric and a nonwoven fabric, and it scatters at least one of the light emitted from the irradiating part and the light from the specimen. For example, if the light scattering part is disposed both between the irradiating part and the specimen and between the specimen and the light receiving part, the light emitted from the irradiating part is scattered by the light scattering part and then applied to the specimen. The light from the specimen caused by the light applied to the specimen is scattered by the light scattering part and then detected by the light receiving part.

According to the study of the inventors or the like, by that the light scattering part is disposed at least one of between the irradiating part and the specimen and between the specimen and the light receiving part, it is possible to reduce a change in the detection value of the light detected by the light receiving part, which is caused by, for example, a shift in relative position relation between the light receiving part and the specimen, in comparison with a case where the light scattering part is not disposed between the irradiating part and the specimen and between the specimen and the light receiving part. Therefore, on the basis of the light detected by the light receiving part, it is possible to stably detect the predetermined type of information, such as a blood flow velocity, on the specimen. As a result, it is possible to increase the reliability of the detection value detected by the light-emitting sensor device.

As explained above, according to the light-emitting sensor device of the present invention, it is provided with the light scattering part disposed at least one of between the irradiating part and the specimen and between the specimen and the light receiving part, so that it is possible to reduce the change in the detection value caused by the shift in relative position relation between the light-emitting sensor device and the specimen. Thus, it is possible to stably detect the predetermined type of information, such as a blood flow velocity, on the specimen.

In one aspect of the light-emitting sensor device of the present invention, the light scattering part includes a fibrous material.

According to this aspect, the light scattering part is made of, for example, a woven fabric or a nonwoven fabric. Thus, by virtue of the light scattering part, it is possible to preferably scatter at least one of the light emitted from the irradiating part and the light from the specimen, and it is possible to surely reduce the change in the detection value caused by the shift in relative position relation between the light-emitting sensor device and the specimen. Moreover, if the light scattering part is made of, for example, a woven fabric or a nonwoven fabric, it is also possible to stably detect the predetermined type of information, such as a blood flow velocity, on the specimen, regardless of a change in power of the specimen being pressed against the light scattering part in the measurement.

In another aspect of the light-emitting sensor device of the present invention, the light scattering part includes foam.

According to this aspect, the light scattering part includes the foam such as a sponge (or a porous body having a plurality of continuous pores therein). Thus, by virtue of the light scattering part, it is possible to preferably scatter at least one of the light emitted from the irradiating part and the light from the specimen, and it is possible to surely reduce the change in the detection value caused by the shift in relative position relation between the light-emitting sensor device and the specimen. Moreover, if the light scattering part is made of, for example, a sponge, it is also possible to stably detect the predetermined type of information, such as a blood flow velocity, on the specimen, regardless of the change in power of the specimen being pressed against the light scattering part in the measurement.

In another aspect of the light-emitting sensor device of the present invention, the light scattering part has a plurality of scattering materials dispersed in a transparent member which can transmit the at least one light, each of the plurality of scattering materials having a refractive index which is different from a refractive index of the transparent member, the plurality of scattering materials being capable of scattering the at least one light.

According to this aspect, by virtue of the light scattering part, it is possible to preferably scatter at least one of the light emitted from the irradiating part and the light from the specimen, and it is possible to surely reduce the change in the detection value caused by the shift in relative position relation between the light-emitting sensor device and the specimen.

In another aspect of the light-emitting sensor device of the present invention, it is further provided with a front plate disposed to face the substrate, on a front surface side where the specimen is disposed with respect to the substrate, the light scattering part being bonded to the front plate by an adhesive which can transmit the at least one light.

According to this aspect, the front plate is a light shielding plate-like member where an exit aperture for transmitting the light emitted from the irradiating part and an entrance aperture for transmitting the light from the specimen are formed. The light scattering part is disposed to cover the surface on the specimen side of the front plate, and it is bonded to the front plate by the adhesive. Thus, for example, by that the specimen touches the light scattering part in the detection, it is possible to prevent that the position of the light scattering part on the light-emitting sensor device is shifted. Here, the adhesive can transmit at least one of the light emitted from the irradiating part and the light from the specimen, so that it has practically little or no adverse influence on the light detected by the light receiving part. Incidentally, here, the expression that "the light scattering part is bonded to the front plate by the adhesive" includes, in effect, not only a case where the light scattering part is bonded to the front plate itself by the adhesive but also a case where the light scattering part is bonded to a protective plate disposed on the upper surface of the front plate.

In another aspect of the light-emitting sensor device of the present invention, it is further provided with a light shielding part, disposed between the irradiating part and the light receiving part on the substrate, for shielding between the irradiating part and the light receiving part from light.

According to this aspect, for example, it is possible to block the light directly going from the irradiating part to the light receiving part, out of the light emitted from the irradiating part (i.e. the light which is emitted from the irradiating part and which goes to the light receiving part without being applied to the specimen). Thus, it is possible to prevent that the light detected by the light receiving part changes due to the light which directly goes from the irradiating part to the light receiving part. Therefore, it is possible to detect the predetermined type of information, such as a blood flow velocity, on the specimen, more highly accurately.

In another aspect of the light-emitting sensor device of the present invention, the irradiating part and the light receiving part are integrated on the substrate.

According to this aspect, the irradiating part and the light receiving part are integrated on the substrate, so that the layout area for each part is reduced, which further allows miniaturization. Due to the miniaturization, it is possible to extend the use of the light-emitting sensor device, such as making it not of a stationary type but a mobile type.

In another aspect of the light-emitting sensor device of the present invention, it is further provided with a calculating part for calculating a blood flow velocity associated with the specimen, on the basis of the detected light.

According to this aspect, by using that the penetration force of light to a living body depends on wavelength, it is possible to measure the blood flow velocity of each of blood vessels which have different depth from the skin surface. Specifically, by applying light to the surface of a living body, the light penetrating into the body is reflected or scattered by red blood cells flowing in the blood vessel, and its wavelength changes due to the Doppler-shift according to the transfer rate of the red blood cells. On the other hand, as for the light reflected or scattered by skin tissue which can be considered immovable with respect to the red blood cells, the light reaches to the light receiving part without any change in the wavelength. By those lights interfering with each other, an optical beat signal corresponding to the Doppler shift amount is detected on the light receiving part. The calculating part performs an arithmetic process, such as frequency analysis, on the optical beat signal, thereby calculating the velocity of the blood flowing in the blood vessel.

In another aspect of the light-emitting sensor device of the present invention, the irradiating part has a semiconductor laser for generating laser light as the light.

According to this aspect, the laser light can be applied by applying a voltage to the semiconductor of the irradiating part such that an electric current flows with a higher value than a laser oscillation threshold value. The laser light has such a character that it has a different penetration force to a living body or the like depending on a difference in wavelength. By using such a character, it is possible to perform the measurement in different depth of the specimen.

The operation and other advantages of the present invention will become more apparent from the embodiment explained below.

As explained in detail above, according to the light-emitting sensor device of the present invention, it is provided with the substrate, the irradiating part, the light receiving part, and the light scattering part. Therefore, it is possible to reduce the change in the detection value caused by the shift in relative position relation between the light-emitting sensor device and the specimen, and thus, it is possible to detect the predetermined type of information, such as a blood flow velocity, on the specimen, highly accurately.

Figure 1:
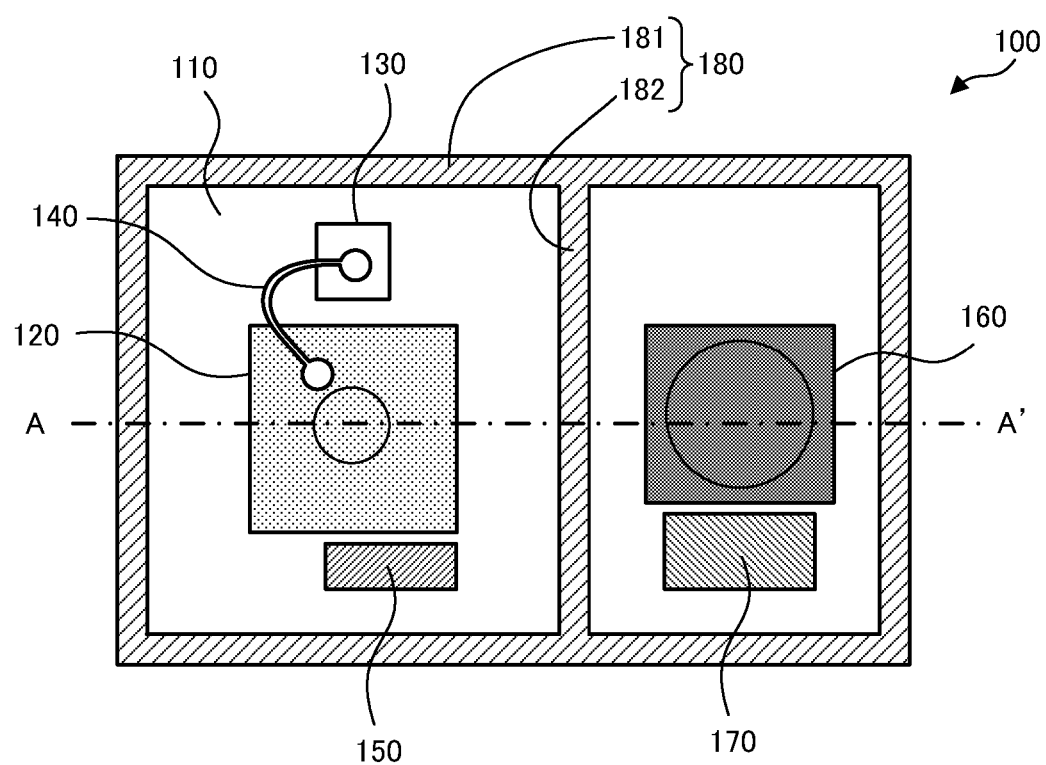
FIG. 1 is a plan view showing the structure of a sensor part of a blood flow sensor device in a first embodiment.

DESCRIPTION OF REFERENCE CODES 100 sensor part
110 sensor part substrate
120 laser diode
150 laser diode drive circuit
160 photodiode
170 photodiode amplifier
180 light shielding wall
190 front plate
195 protective plate
200 scatterer
310 A/D converter
320 blood flow velocity DSP

BEST MODE FOR CARRYING OUT THE INVENTION

Hereinafter, an embodiment of the present invention will be explained with reference to the drawings. Incidentally, the embodiment below exemplifies a blood flow sensor device, which is one example of the light-emitting sensor device of the present invention.

First Embodiment

A blood flow sensor device in a first embodiment will be explained.

Firstly, the structure of a sensor part of the blood flow sensor device in the first embodiment will be explained with reference to FIG. 1 to FIG. 4.

Figure 2:
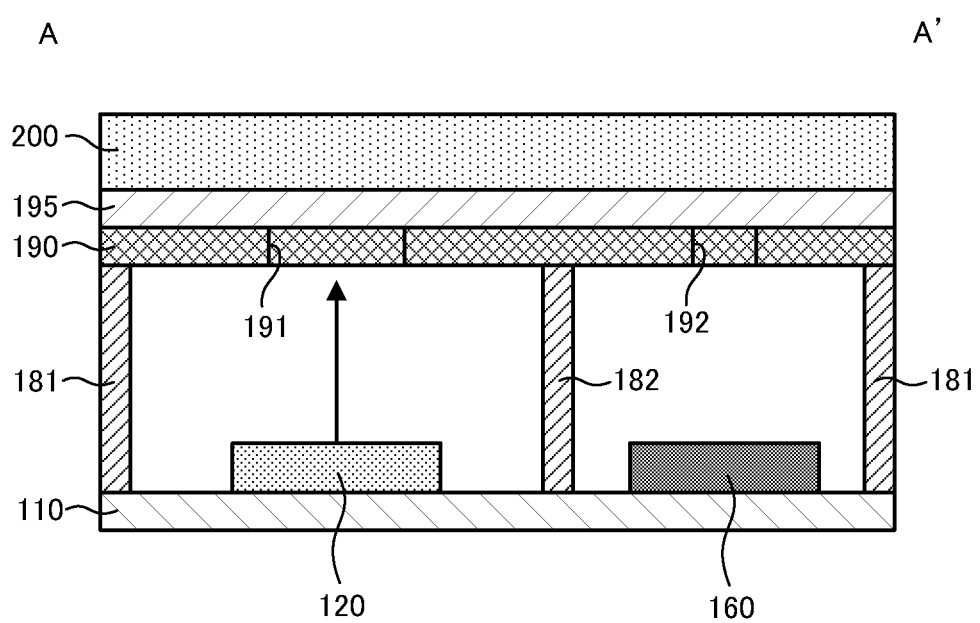
FIG. 2 is an A-A' cross sectional view in FIG. 1.

FIG. 1 is a plan view showing the structure of the sensor part of the blood flow sensor device in the first embodiment. FIG. 2 is an A-A' cross sectional view in FIG. 1. Incidentally, in FIG. 1, for convenience of explanation, the illustration of a front plate 190, a protective plate 195, and a scatterer 200 shown in FIG. 2 is omitted.

As shown in FIG. 1 and FIG. 2, a sensor part 100 of the blood flow sensor device in the first embodiment is provided with a sensor part substrate 110, a laser diode 120, an electrode 130, a wire line 140, a laser diode drive circuit 150, a photodiode 160, a photodiode amplifier 170, a light shielding wall 180, a front plate 190, a protective plate 195, and a scatterer 200.

The sensor part substrate 110 is made of a semiconductor substrate, such as a silicon substrate. On the sensor part substrate 110, the laser diode 120, the laser diode drive circuit 150, the photodiode 160, and the photodiode amplifier 170 are integrated and disposed.

The laser diode 120 is one example of the "irradiating part" of the present invention, and it is a semiconductor laser for emitting laser light. The laser diode 120 is electrically connected to the electrode 130 through the wire line 140. The electrode 130 is electrically connected to an electrode pad (not illustrated) disposed on the bottom of the sensor part substrate 100 by wiring (not illustrate) which penetrates the sensor part substrate 110, and it can drive the laser diode 120 by current injection from the exterior of the sensor part 100.

The laser diode drive circuit 150 is a circuit for controlling the drive of the laser diode 120, and it controls the amount of an electric current injected to the laser diode 120.

The photodiode 160 is one example of the "light receiving part" of the present invention, and it functions as a light detector for detecting the light reflected or scattered from a specimen (more specifically, the light scattered by the scatterer 200 described later). Specifically, the photodiode 160 can obtain information about light intensity by converting the light to an electric signal. The photodiode 160 is disposed in parallel with the laser diode 120 on the sensor part substrate 110.

The photodiode amplifier 170 is an amplifier circuit for amplifying the electric signal obtained by the photodiode 160. The photodiode amplifier 170 is electrically connected to the electric pad (not illustrated) disposed on the bottom of the sensor part substrate 100 by the wiring (not illustrate) which penetrates the sensor part substrate 110, and it can output the amplified electric signal to the exterior. The photodiode amplifier 170 is electrically connected to an A/D (Analog to Digital) converter 310 (refer to FIG. 5 described later) disposed in the exterior of the sensor part 100.

The light shielding wall 180 is formed in a wall shape on the sensor part substrate 110, including a light shielding material. The light shielding wall 180 has: a first light shielding part 181 formed along a circumference on the sensor part substrate 110; and a second light shielding part 182 formed between the laser diode 120 and the photodiode 160 on the sensor part substrate 110. The first light shielding part 181 is formed to surround all the laser diode 120, the electrode 130, the wire line 140, the laser diode drive circuit 160, the photo diode 160, and the photodiode amplifier 170, viewed in a two-dimensional manner on the sensor part substrate 110. By virtue of the first light shielding part 181, it is possible to prevent the light from the surroundings of the sensor part 100 from entering into the sensor part 100 (i.e. inner than the first light shielding part 181 on the sensor part substrate 110). The second light shielding part 182 is formed to connect a portion formed along one side of the sensor part substrate 110 of the first light shielding part 181 and a portion formed along the other side opposed to the one side of the first light shielding part 181, between the laser diode 120 and the photodiode 160 on the sensor part substrate 110. By virtue of the second light shielding part 182, it is possible to shield between the laser diode 120 and the photodiode 160 from the light. Thus, for example, it is possible to block the light going to the photodiode 160 as it is, without being applied to the specimen, out of the light emitted from the laser diode 120. In other words, it is possible to prevent the light which does not have to be detected by the photodiode 160 from entering the photodiode 160 from the laser diode 120 side to the photodiode 160 side on the sensor part substrate 110, thereby increasing the detection accuracy.

The front plate 190 is a substrate including a light shielding material, and it is disposed above the laser diode 120, the photodiode 170, and the like (in other words, such that it faces the sensor part substrate 110 via the light shielding wall 180). Incidentally, the plate thickness of the front plate 190 is, for example, about 300 um.

Figure 3:
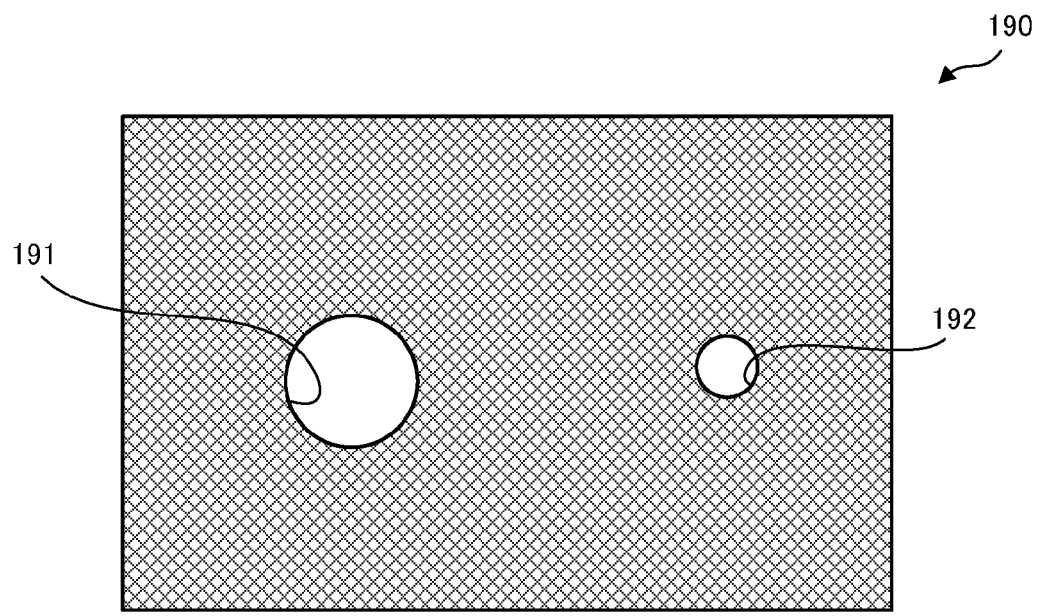
FIG. 3 is a plan view showing the structure of a front plate of the blood flow sensor device in the first embodiment.

FIG. 3 is a plan view showing the structure of the front plate of the blood flow sensor device in the first embodiment.

As shown in FIG. 2 and FIG. 3, in the front plate 190, an exit aperture 191 for letting out or emitting the light from the laser diode 120 to the exterior is opened, and an entrance aperture 192 for letting in the light reflected or scattered from the specimen is formed in a pinhole shape. The pinhole-shaped formation of the entrance aperture 192 allows the incidence of only the light from directly above (i.e. in a top-to-bottom direction in FIG. 2). Thus, it is possible to prevent the light that does not have to be detected from entering the photodiode 160, thereby increasing the detection accuracy. Incidentally, the diameter of the entrance aperture 192 formed in the pinhole shape is, for example, about 40 um.

In FIG. 2, the protective plate 195 is disposed on the upper surface side of the front plate 190. The protective plate 195 is made of a transparent substrate and can transmit the light from the laser diode 120 and the light from the specimen. The protective plate 195 is disposed to overlap the entire surface of the front plate 190. As the protective plate 195, for example, a resin substrate, a glass substrate, or the like can be used. The protective plate 195 can increase the durability of the sensor part 100.

The scatterer 200 is one example of the "light scattering part" of the present invention, and it is made of a fibrous material, such as a woven fabric and a nonwoven fabric. The scatterer 200 is bonded to the protective plate 195 by an adhesive which can transmit the light from the laser diode 120 and the light from the specimen. Thus, in the measurement, it is possible to prevent that the specimen touches the scatterer 200 and shifts the position of the scatterer 200 on the sensor part 100.

Figure 4:
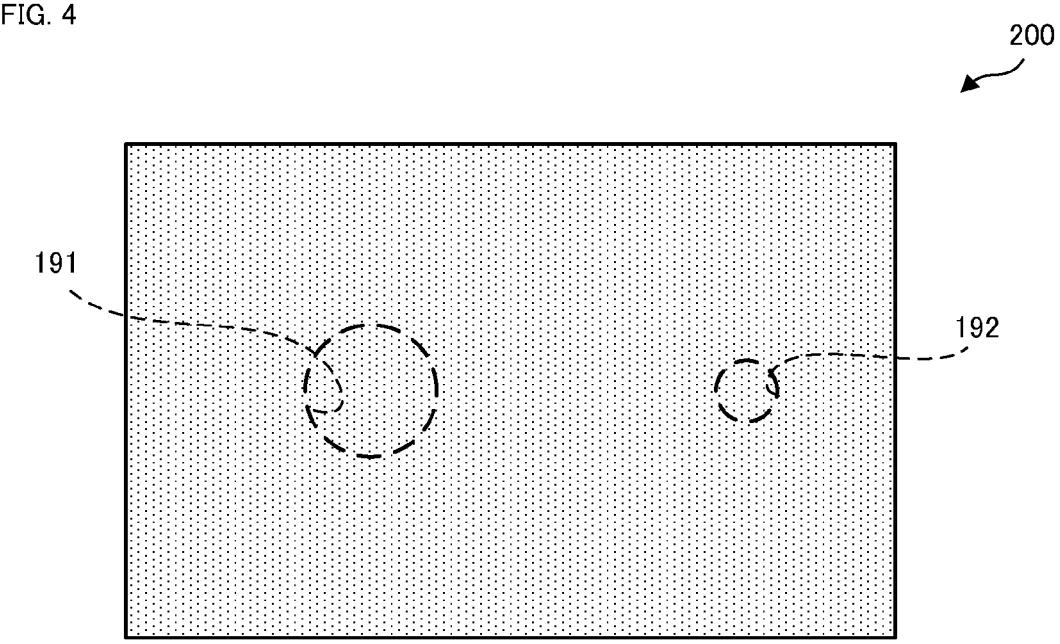
FIG. 4 is a plan view showing the structure of a scatterer of the blood flow sensor device in the first embodiment.

FIG. 4 is a plan view showing the structure of the scatterer of the blood flow sensor device in the first embodiment.

In FIG. 2 and FIG. 4, the scatterer 200 is formed to overlap the entire surface of the protective plate 195, on the upper surface side of the protective plate 195. The scatterer 200 is made of the fibrous material as described above, so that it can scatter the light from the laser diode 120 and the light reflected or scattered from the specimen. It is only necessary for the scatterer 200 to scatter the light from the laser diode 120 and the light reflected or scattered from the specimen. The scatterer 200 may be made of not only the fibrous material but also foam, such as a sponge, and a porous body. Alternatively, the scatterer 200 may be made by dispersing small particles made of polymer resin, glass, or the like, which have different refraction indexes from that of a transparent material, in the transparent material made of plastic, glass, or the like. Incidentally, an effect by the scatterer 200 will be detailed later. In the embodiment, in particular, the sensor part 100 is provided with the scatterer 200, so that it is possible to stably detect the blood flow velocity of the specimen.

Next, the structure of the entire blood flow sensor device in the first embodiment will be explained with reference to FIG. 5.

Figure 5:
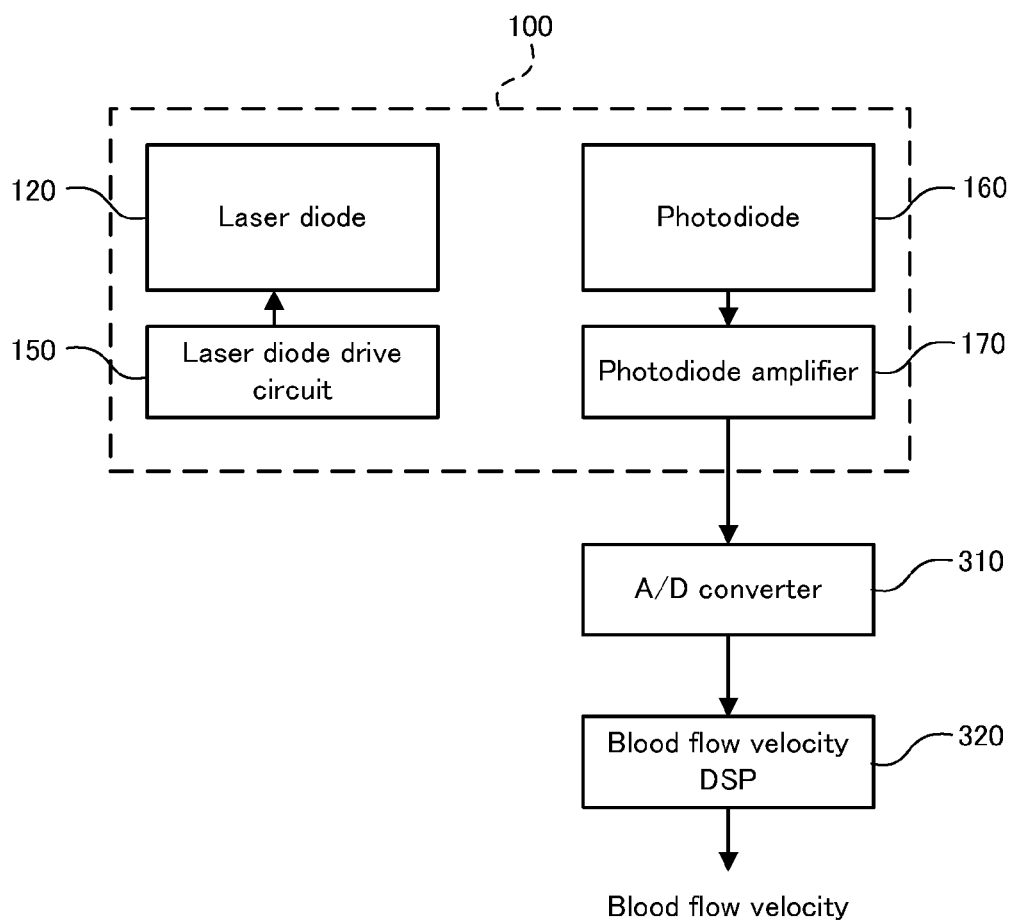
FIG. 5 is a block diagram showing the structure of the blood flow sensor device in the first embodiment.

FIG. 5 is a block diagram showing the structure of the blood flow sensor device in the first embodiment.

In FIG. 5, the blood flow sensor device in the first embodiment is provided with an A/D converter 310 and a blood flow velocity digital signal processor (DSP) 320, in addition to the aforementioned sensor part 100.

The A/D converter 310 converts the electric signal outputted from the photodiode amplifier 170, from an analog signal to a digital signal. In other words, the electric signal obtained by the photodiode 160 is amplified by the photodiode amplifier 170, and then it is converted to the digital signal by the A/D converter 310. The A/D converter 310 outputs the digital signal to the blood flow velocity DSP 320.

The blood flow velocity DSP 320 is one example of the "calculating part" of the present invention, and it calculates the blood flow velocity by performing a predetermined arithmetic process on the digital signal inputted from the A/D converter 310.

Next, the measurement of the blood flow velocity by the blood flow sensor device in the first embodiment will be explained with reference to FIG. 6 and FIG. 7 in addition to FIG. 5.

Figure 6:
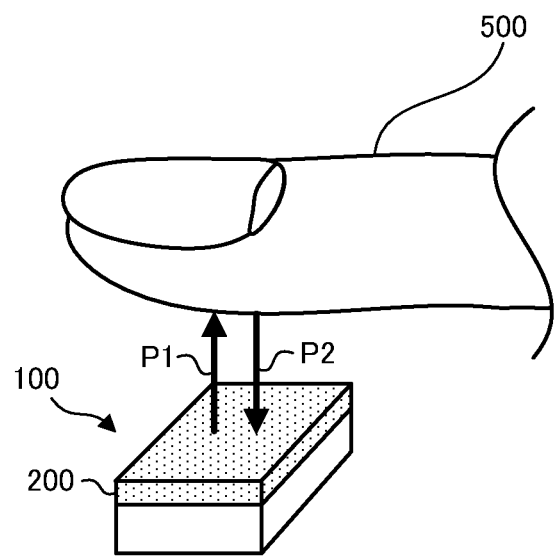
FIG. 6 is a conceptual view showing one example of how to use the blood flow sensor device in the first embodiment.

FIG. 6 is a conceptual view showing one example of how to use the blood flow sensor device in the first embodiment. FIG. 7 is a cross sectional view showing a human subcutaneous structure.

As shown in FIG. 6, the blood flow sensor device in the first embodiment measures the blood flow velocity by irradiating a fingertip 500, which is one example of the specimen, with laser light with a predetermined wavelength (e.g. infrared light with a wavelength of 780 nm, 830 nm, or 1300 nm) by using the laser diode 120. At this time, a portion irradiated with the laser light is more desirably a portion in which blood capillaries are distributed densely in a position relatively close to the epidermis (e.g. hand, leg, face, ear, or the like). Incidentally, in FIG. 6 and FIG. 7, an arrow P1 conceptually shows the light emitted from the sensor part 100. Moreover, in the measurement of the blood flow velocity, the blood flow sensor device in the first embodiment is typically used in the condition that the fingertip 500 touches the upper surface of the sensor part 100 (i.e. the upper surface of the scatterer 200); however, for convenience of explanation, FIG. 6 shows a gap between the fingertip 500 and the sensor part 100. However, according to the blood flow sensor device in the first embodiment, it is possible to measure the blood flow velocity even if the fingertip 500 does not touch the upper surface of the sensor part 100.

Figure 7:
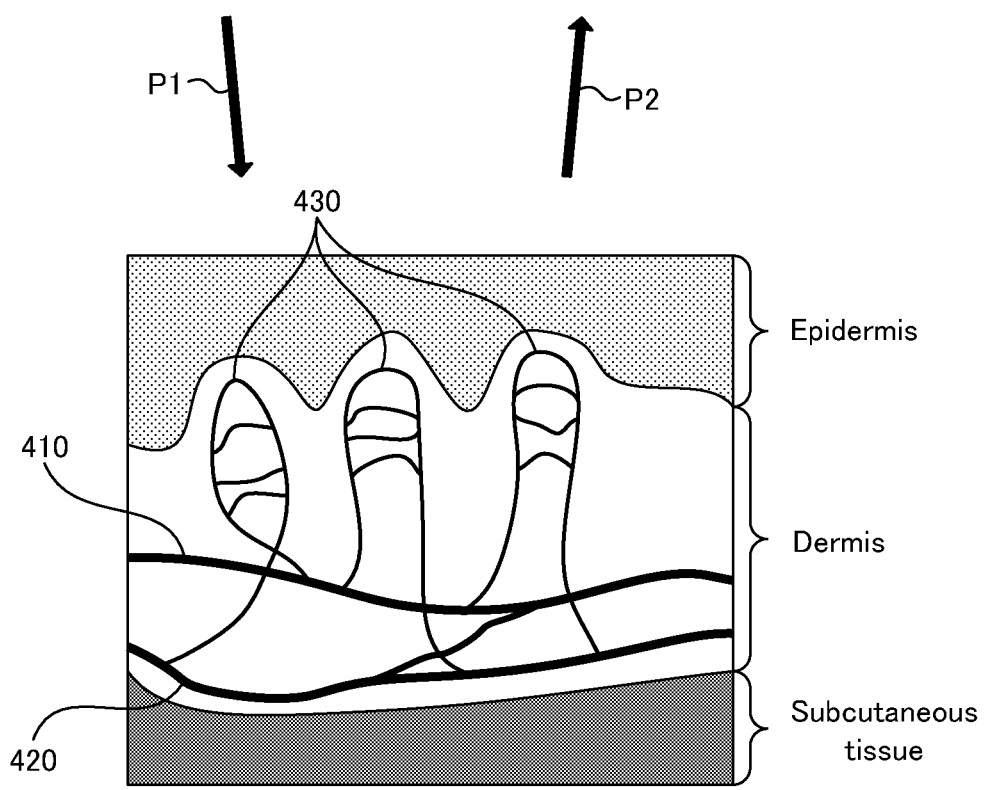
FIG. 7 is a cross sectional view showing a human subcutaneous structure.

Here, as shown in FIG. 7, in the human subcutaneous structure, an anteriole 410 and a venule 420 are distributed in the dermis located between the epidermis and the subcutaneous tissue. Then, blood capillaries 430 branching from the anteriole 410 are distributed toward to the vicinity of the epidermis, and one ends are connected to the venule 420.

In FIG. 6 and FIG. 7, the laser light applied to the fingertip 500 penetrates to depth according to its wavelength, and it is reflected or scattered by the body tissue of the fingertip 500, such as blood flowing in blood vessels like the blood capillaries or the like and skin cells which constitute the epidermis. In general, the light with a longer wavelength allows the measurement in a deeper portion. Incidentally, in FIG. 6 and FIG. 7, an arrow P2 conceptually shows the light entering the sensor part 100 after being reflected or scattered by the body tissue of the fingertip 500. Then, the Doppler shift occurs in the light reflected or scattered by red blood cells flowing in the blood vessels, and the wavelength of the light changes depending on the transfer rate of the red blood cells or the rate at which the blood flows (i.e. the blood flowing velocity). On the other hand, as for the light reflected or scattered by the skin cells or the like which can be considered immovable with respect to the red blood cells, the wavelength of the light does not change. By those lights interfering with each other, an optical beat signal corresponding to the Doppler shift amount is detected on the photodiode 160 (refer to FIG. 5). The blood flow velocity DSP 320 (refer to FIG. 5) performs frequency analysis on the optical beat signal detected by the photodiode 160 and calculates the Doppler shift amount, thereby calculating the blood flow velocity.

Next, the scatterer of the blood flow sensor device in the first embodiment will be explained together with the operations of the blood flow sensor device in the first embodiment, with reference to FIG. 8 in addition to FIG. 5.

Figure 8:
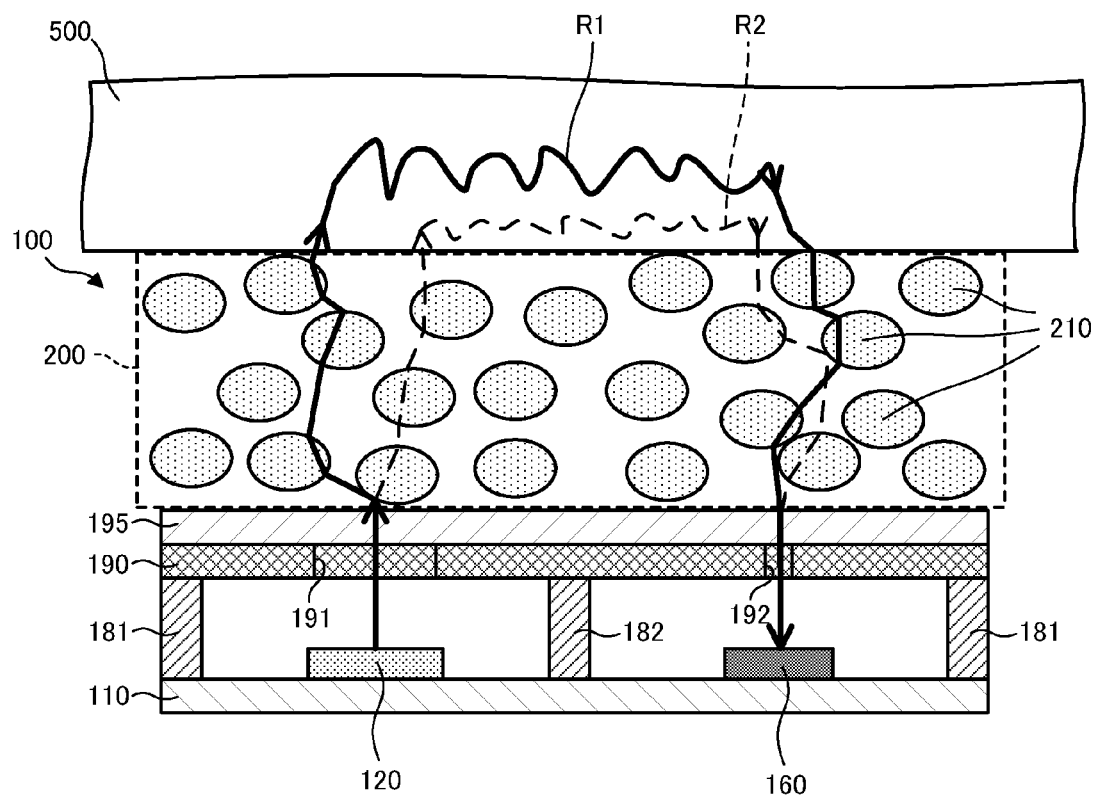
FIG. 8 is a conceptual view showing one example of optical paths in the scatterer and a specimen on the blood flow sensor device in the first embodiment.

FIG. 8 is a conceptual view showing one example of optical paths in the scatterer and the specimen on the blood flow sensor device in the first embodiment.

In FIG. 8, in the operation of the blood flow sensor device in the first embodiment, firstly, the light with a predetermined wavelength is emitted from the laser diode 120, under the control by the laser diode drive circuit 150 (refer to FIG. 5). The emitted light passes through the exit aperture 191 of the front plate 190, penetrates through the protective plate 195, and enters the scatterer 200. The light entering the scatterer 200 is scattered within the scatterer 200 and then enters the fingertip 500, which is one example of the specimen. More specifically, the light entering the scatterer 200 is reflected on the surfaces of the fibrous materials 210 which constitute the scatterer 200, is transmitted through the fibrous materials 210, or is refracted on the surfaces of the fibrous materials 210. The light entering the scatterer 200, as described above with reference to FIG. 6 and FIG. 7, penetrates to the depth according to its wavelength, and it is reflected or scattered by the body tissue of the fingertip 500, such as blood flowing in blood vessels and skin cells. The Doppler shift occurs in the light reflected or scattered by the red blood cells flowing in the blood vessels, and the wavelength of the light changes depending on the transfer rate of the red blood cells. On the other hand, as for the light reflected or scattered by stationary tissue, such as the skin cells which can be considered immovable with respect to the red blood cells, the wavelength of the light does not change. Incidentally, in FIG. 8, a route R1 shows one example of the optical path in the scatterer 200 and the fingertip 500 with regard to the light scattered or reflected by the red blood cells in the fingertip 500, and a route R2 shows one example of the optical path in the scatterer 200 and the fingertip 500 with regard to the light scattered or reflected by the stationary tissue, such as the skin cells, in the fingertip 500. The light reflected or scattered in the fingertip 500 as described above enters the scatterer 200 again. The light entering from the fingertip 500 to the scatterer 200 is scattered again within the scatterer 200, penetrates through the protective plate 195, and enters the photodiode 160 via the entrance aperture 192 of the front plate 190. By that the light reflected or scattered by the red blood cells and the light scattered or reflected by the stationary tissue, which are included in the light entering the photodiode 160, interfere with each other, the optical beat signal corresponding to the Doppler shift amount is detected on the photodiode 160.

Here, particularly in the embodiment, the sensor part 100 is provided with the scatterer 200, so that the light emitted from the laser diode 120 is reflected or scattered on the fingertip 500, which is one example of the specimen, and it is scattered by the scatterer 200 in the middle of the route to the photodiode 150, as described above. By this, as explained later, it is possible to stably detect the blood flow velocity. Incidentally, in the embodiment, the scatterer 200 is disposed to overlap the entire surface of the protective plate 195 such that the light emitted from the laser diode 120 is scattered before the light enters the fingertip 500 and such that the light emitted from the fingertip 500 after being reflected or scattered in the fingertip 500 is scattered before the light enters the photodiode 160. However, the scatterer 200 may be disposed only on the laser diode 120 side on the protective plate 195 so that only the light emitted from the laser diode 120 is scattered before the light enters the fingertip 500. Alternatively, the scatterer 200 may be disposed only on the photodiode 160 side on the protective plate 195 so that the light emitted from the fingertip 500 after being reflected or scattered in the fingertip 500 is scattered before the light enters the photodiode 160. In any case, the scattering of the light in the scatterer 200 can appropriately provide an effect of increasing stability in the detection of the blood flow velocity.

Moreover, the sensor part 100 of the blood flow sensor device in the first embodiment has a relatively simple structure, which facilitates mass production. In other words, the sensor par 100 has such a relatively simple structure that the scatterer 200 is provided for a sensor part main body, which is provided with: the sensor part substrate 110 on which the laser diode 120, the photodiode 160, and the like are integrated; the light shielding wall 180; the front plate 190; and the protective plate 195. Thus, the blood flow sensor device in the first embodiment is suitable for the mass production.

In addition, particularly in the embodiment, the sensor part 100 is provided with the scatterer 200, so that it is possible to almost or completely eliminate the risk of the laser exposure of the specimen by the laser light emitted from the laser diode 120. In other words, since the light emitted from the laser diode 120 is scattered by the scatterer 200, only the scattered light is let out or emitted to the exterior of the sensor part 100. Thus, the risk of the laser exposure of the specimen almost or completely disappears. Incidentally, in the blood flow sensor device in the first embodiment, it is enough to perform an appropriate measurement if the laser light emitted from the laser diode 120 has a power of about several milliwatt at most. Even if the laser light emitted from the laser diode 120 directly enters the specimen without being scattered by the scatterer 200, although there is practically almost no risk of the laser exposure of the specimen, it is possible to further reduce the risk of the laser exposure by being scattered by the scatterer 200.

First Modified Example

A blood flow sensor apparatus in a first modified example will be explained with reference to FIG. 9.

Figure 9:
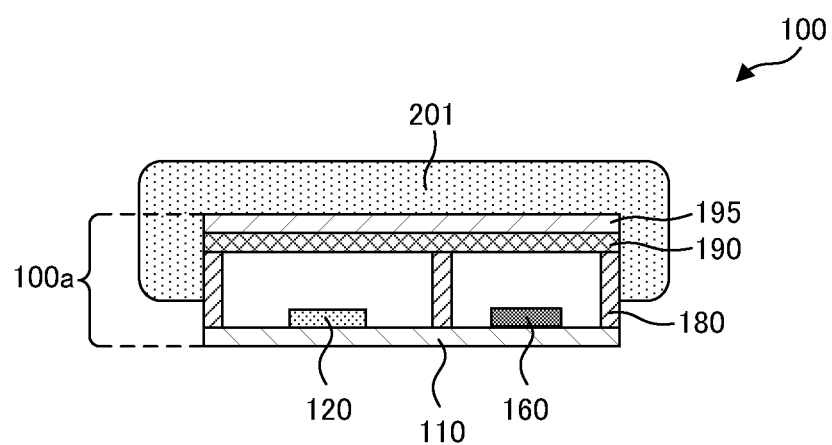
FIG. 9 is a cross sectional view having the same concept as in FIG. 2 in a first modified example.

FIG. 9 is a cross sectional view having the same concept as in FIG. 2 in the first modified example. Incidentally, in FIG. 9, the same constituents as those in the first embodiment shown in FIG. 1 to FIG. 8 will carry the same reference numerals, and the explanation thereof will be omitted, as occasion demands.

In FIG. 9, the blood flow sensor apparatus in the first modified example is different from the blood flow sensor apparatus in the first embodiment described above in the point that it is provided with a scatterer 201 instead of the scatterer 200 in the first embodiment described above, and it is constructed in substantially the same manner as the blood flow sensor apparatus in the first embodiment described above in other points.

As shown in FIG. 9, the scatterer 201 is disposed to wrap around the protective plate 195, the front plate 190, and the light shielding wall 180 from the upper surface side of the protective plate 195. The scatterer 201 is made of a fibrous material, such as a woven fabric and a nonwoven fabric, as in the scatterer 200 in the first embodiment. Thus, it is possible to protect a sensor part main body 100a (i.e. a portion other than the scatterer 201 out of the sensor part 100) by using the scatterer 201. In other words, it is possible to reduce the situation that the sensor part main body 100a is exposed to the exterior to cause the sensor part main body 100a to get dirty and damaged, by virtue of the scatterer 201. Incidentally, the scatterer 201 may wrap around the entire sensor part main body 100a. In this case, it is possible to increase the effect of protecting the sensor part main body 100a by virtue of the scatterer 201.

Second Modified Example

A blood flow sensor apparatus in a second modified example will be explained with reference to FIG. 10.

Figure 10:
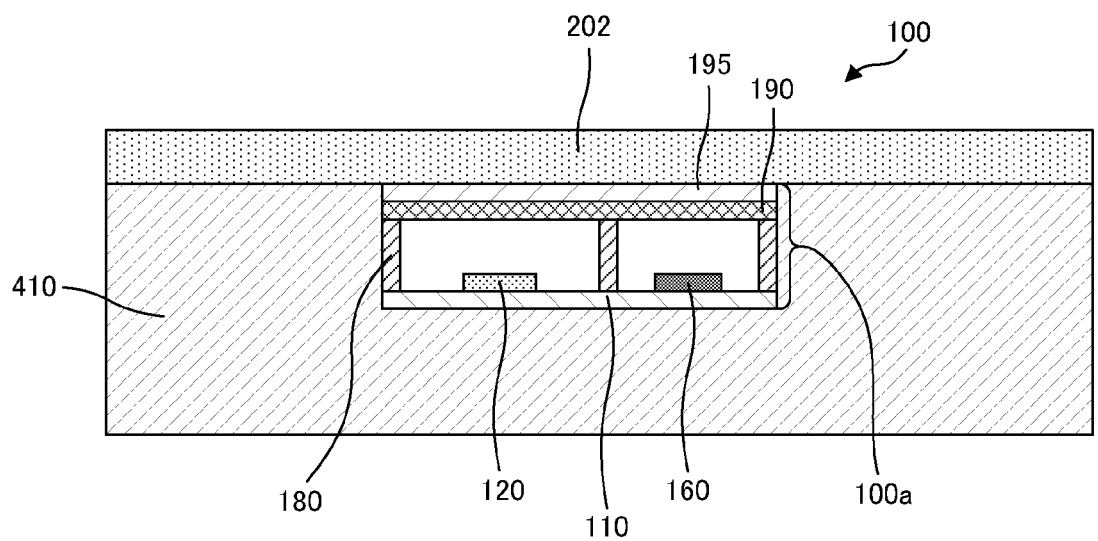
FIG. 10 is a cross sectional view having the same concept as in FIG. 2 in a second modified example.

FIG. 10 is a cross sectional view having the same concept as in FIG. 2 in the second modified example. Incidentally, in FIG. 10, the same constituents as those in the first embodiment shown in FIG. 1 to FIG. 8 will carry the same reference numerals, and the explanation thereof will be omitted, as occasion demands.

In FIG. 10, the blood flow sensor apparatus in the second modified example is different from the blood flow sensor apparatus in the first embodiment described above in the point that it is provided with a scatterer 202 instead of the scatterer 200 in the first embodiment described above and further with a structure 410, and it is constructed in substantially the same manner as the blood flow sensor apparatus in the first embodiment described above in other points.

As shown in FIG. 10, in the sensor part 100 of the blood flow sensor apparatus in the second modified example, the sensor part main body 100a (i.e. a portion other than the scatterer 202 out of the sensor part 100; namely, the sensor part substrate 110, the laser diode 120 (and the laser diode drive 150), the photodiode 160 (and the photodiode amplifier 170), the light shielding wall 180, the front plate 190 and the protective plate 195) is embedded or implanted within the structure 410, with the protective plate 195 exposed from the upper surface side of the structure 410, and the scatterer 202 is disposed to overlap all the upper surfaces of the structure 410 and the protective plate 195. The structure 410 can be formed of, for example, resin, glass, metal, or the like. The scatterer 202 is made of a fibrous material, such as a woven fabric and a nonwoven fabric, as in the scatterer 200 in the first embodiment.

According to the blood flow sensor apparatus in the second modified example as constructed above, it is possible to protect the sensor part main body 100a by using the scatterer 202 and the structure 410. Moreover, the structure 410 can be protected by the scatterer 202 from the upper surface side thereof.

Third Modified Example

A blood flow sensor apparatus in a third modified example will be explained with reference to FIG. 11.

Figure 11:
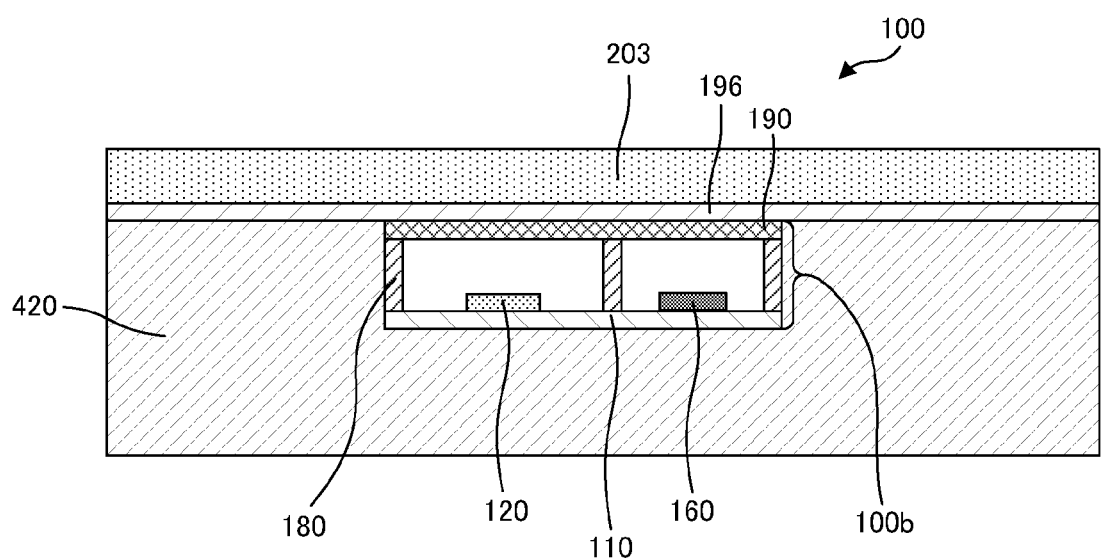
FIG. 11 is a cross sectional view having the same concept as in FIG. 2 in a third modified example.

FIG. 11 is a cross sectional view having the same concept as in FIG. 2 in the third modified example. Incidentally, in FIG. 11, the same constituents as those in the first embodiment shown in FIG. 1 to FIG. 8 will carry the same reference numerals, and the explanation thereof will be omitted, as occasion demands.

In FIG. 11, the blood flow sensor apparatus in the third modified example is different from the blood flow sensor apparatus in the first embodiment described above in the point that it is provided with a protective plate 196 and a scatterer 203 instead of the protective plate 195 and the scatterer 200 in the first embodiment described above, respectively, and further with a structure 420, and it is constructed in substantially the same manner as the blood flow sensor apparatus in the first embodiment described above in other points.

As shown in FIG. 11, in the sensor part 100 of the blood flow sensor apparatus in the third modified example, a sensor part main body 100b (i.e. a portion other than the scatterer 203 and the protective plate 196 out of the sensor part 100; namely, the sensor part substrate 110, the laser diode 120 (and the laser diode drive 150), the photodiode 160 (and the photodiode amplifier 170), the light shielding wall 180 and the front plate 190) is embedded or implanted within the structure 420, with the protective plate 196 exposed from the upper surface side of the structure 420, and the protective plate 196 is disposed to overlap all the upper surfaces of the structure 420 and the front plate 190, and the scatterer 203 is disposed to overlap the upper surface of the protective plate 196. The structure 420 can be formed of, for example, resin, glass, metal, or the like. The scatterer 203 is made of a fibrous material, such as a woven fabric and a nonwoven fabric, as in the scatterer 200 in the first embodiment.

According to the blood flow sensor apparatus in the third modified example as constructed above, it is possible to protect the sensor part main body 100a by using the scatterer 203, the protective plate 196, and the structure 420. Moreover, the structure 420 can be protected by the protective plate 196 and the scatterer 203 from the upper surface side thereof.

Fourth Modified Example

A blood flow sensor apparatus in a fourth modified example will be explained with reference to FIG. 12.

Figure 12:
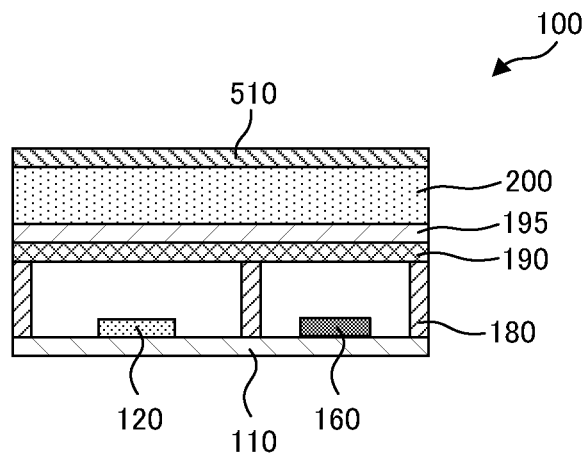
FIG. 12 is a cross sectional view having the same concept as in FIG. 2 in a fourth modified example.

FIG. 12 is a cross sectional view having the same concept as in FIG. 2 in the fourth modified example. Incidentally, in FIG. 12, the same constituents as those in the first embodiment shown in FIG. 1 to FIG. 8 will carry the same reference numerals, and the explanation thereof will be omitted, as occasion demands.

In FIG. 12, the blood flow sensor apparatus in the fourth modified example is different from the blood flow sensor apparatus in the first embodiment described above in the point that it is provided further with a protective member 510, and it is constructed in substantially the same manner as the blood flow sensor apparatus in the first embodiment described above in other points.

As shown in FIG. 12, the protective member 510 is disposed to overlap the upper surface of the scatterer 200 (in other words, a surface opposed to the specimen in the scatterer 200). The protective member 510 is made of a transparent substrate, and it can transmit the light from the laser diode 120 and the light reflected or scattered from the specimen. As the protective member 510, for example, a resin substrate, a glass substrate, or the like can be used.

Thus, it is possible to the situation that the scatterer 200 is exposed to the exterior, or the specimen touches the scatterer 200 to cause the scatterer 200 to get dirty and damaged, by virtue of the protective member 510. In particular, in a case where the scatterer 200 is formed of foam, such as a sponge, and a porous body, the scatterer 200 tends to get dirty relatively, so that it is extremely useful in practice that the scatterer 200 can be protected by the protective member 510 as described above.

Next, the effect by the scatterer of the blood flow sensor device in the first embodiment will be detailed with reference to FIG. 13 to FIG. 17.

Figure 13:
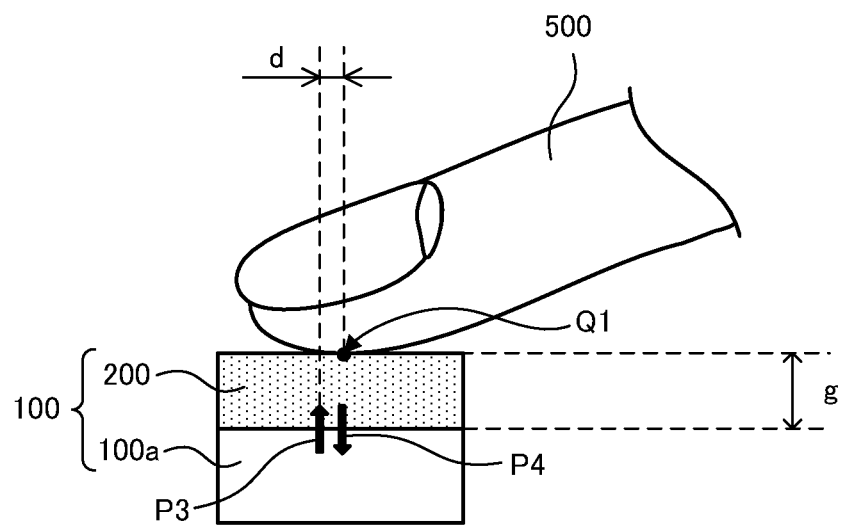
FIG. 13 is a schematic diagram showing a position relation between the sensor part and the specimen in the measurement of a blood flow velocity by the blood flow sensor device in the first embodiment.
Figure 14:
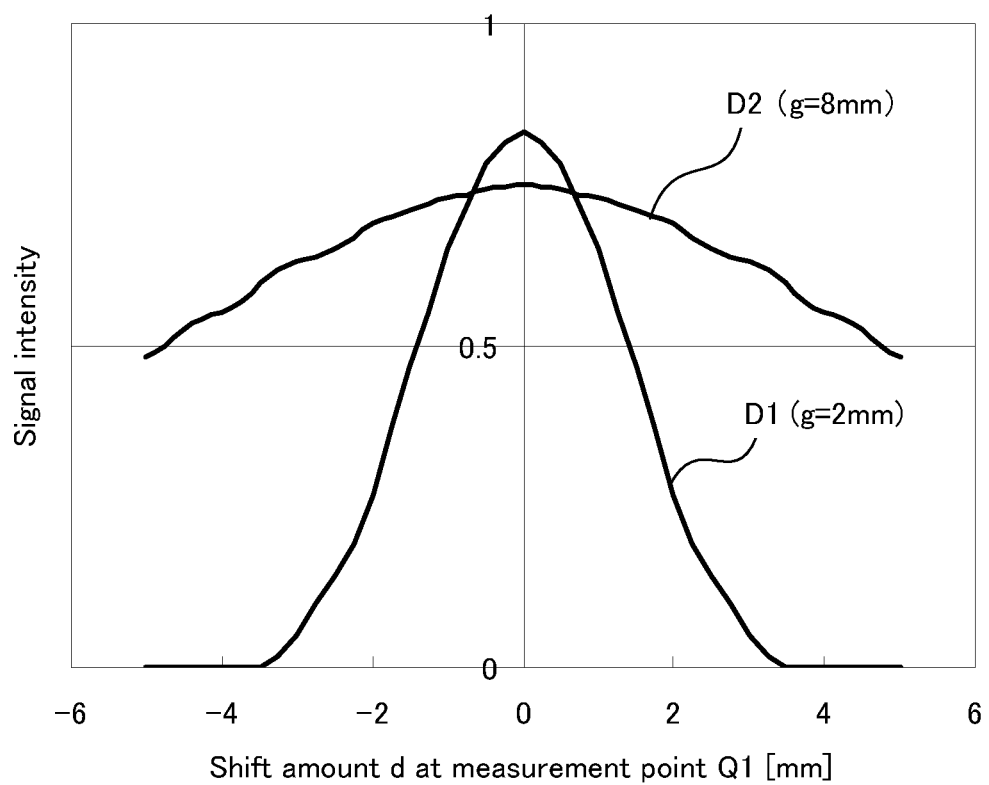
FIG. 14 is a graph showing a relation between a shift amount from a laser diode at a measurement point and signal intensity of an optical beat signal in the measurement of the blood flow velocity by the blood flow sensor device in the first embodiment.

FIG. 13 is a schematic diagram showing a position relation between the sensor part and the specimen in the measurement of the blood flow velocity by the blood flow sensor device in the first embodiment. FIG. 14 is a graph showing a relation between a shift amount from the laser diode at a measurement point and signal intensity of the optical beat signal in the measurement of the blood flow velocity by the blood flow sensor device in the first embodiment.

FIG. 14 shows the relation between a shift amount d from the laser diode 120 at a measurement point Q1 (refer to FIG. 13) and signal intensity of the optical beat signal detected by the photodiode 160, in a case where the blood flow velocity of the fingertip 500, which is one example of the specimen, is measured by using the blood flow sensor device in the first embodiment. Incidentally, in this measurement, a towel fiber is used as the scatterer 200.

Here, in FIG. 13, the measurement point Q1 is a point of the fingertip 500 with the closest distance from the photodiode 160. The shift amount d is the amount of shift from the laser diode 120 at the measurement point Q1 (more accurately, a distance between the measurement point Q1 and a portion of the laser diode 120 where the light emits in a case where the sensor 100 is viewed from directly above. A distance g is a distance between the upper surface of the sensor part main body 100a (i.e. a portion other than the scatterer 200 out of the sensor part 100) and the measurement point Q1. In the measurement of the blood flow velocity, the fingertip 500 touches the scatterer 200, so that the distance g almost or completely matches the thickness of the scatterer 200. Incidentally, in FIG. 13, an arrow P3 conceptually shows the light emitted from the laser diode 120, and an arrow P4 conceptually shows the light entering the photodiode 160.

In FIG. 14, data D1 shows the relation between the shift amount d and the signal intensity of the optical beat signal, in a case where the blood flow velocity is measured with a distance g of 2 mm between the upper surface of the sensor part main body 100a and the measurement point Q1 (in other words, with a thickness of the scatterer 200 of 2 mm). Data D2 shows the relation between the shift amount d and the signal intensity of the optical beat signal, in a case where the blood flow velocity is measured with a distance g of 8 mm between the upper surface of the sensor part main body 100a and the measurement point Q1 (in other words, with a thickness of the scatterer 200 of 8 mm).

Figure 15:
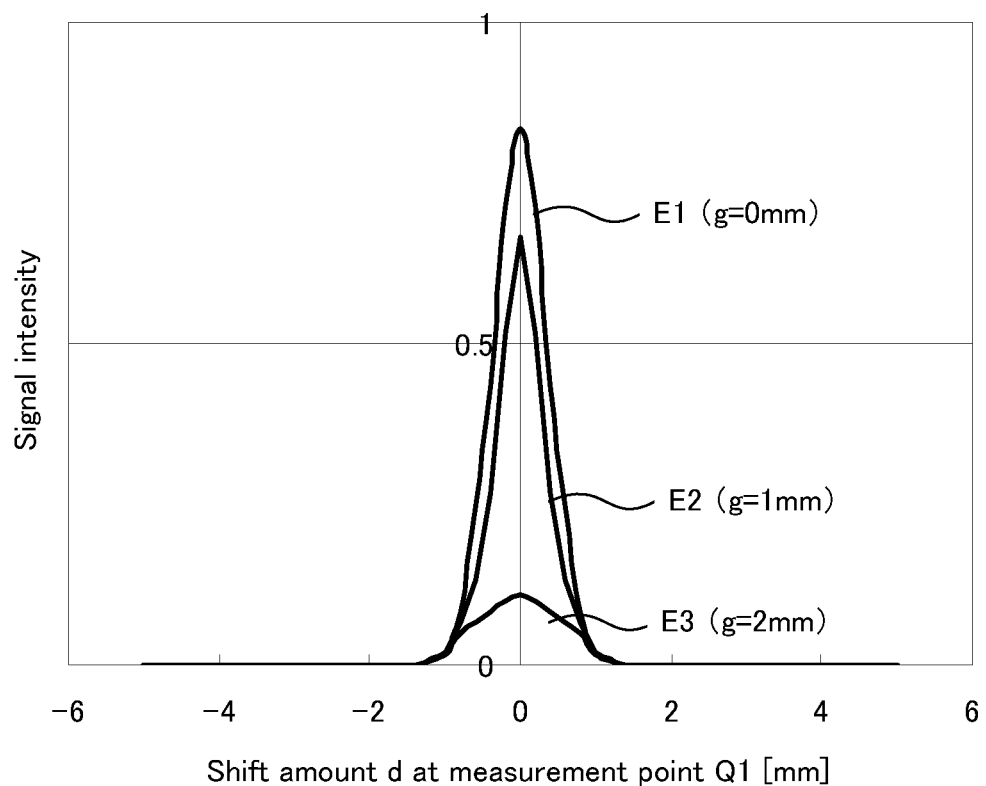
FIG. 15 is a graph showing a relation between a shift amount from a laser diode at a measurement point and signal intensity of an optical beat signal in the measurement of the blood flow velocity by a blood flow sensor device in a comparative example.

FIG. 15 is a graph showing a relation between a shift amount from a laser diode at a measurement point and signal intensity of an optical beat signal in the measurement of the blood flow velocity by a blood flow sensor device in a comparative example. Here, the blood flow sensor device in the comparative example is different from the blood flow sensor device in the first embodiment in the point that it is not provided with the scatterer 200, and it is constructed in substantially the same manner as the blood flow sensor apparatus in the first embodiment described above in other points. In other words, in FIG. 13, the sensor part of the blood flow sensor device in the comparative example corresponds to the sensor part main body 100a of the blood flow sensor apparatus in the first embodiment.

In FIG. 15, data E1 shows the relation between the shift amount d and the signal intensity of the optical beat signal, in a case where the blood flow velocity is measured with a distance g of 0 mm between the upper surface of the sensor part of the blood flow sensor device in the comparative example and the measurement point Q1 (in other words, when the fingertip 500 touches the upper surface of the sensor part of the blood flow sensor device in the comparative example). Data E2 shows the relation between the shift amount d and the signal intensity of the optical beat signal, in a case where the blood flow velocity is measured with a distance g of 1 mm between the upper surface of the sensor part of the blood flow sensor device in the comparative example and the measurement point Q1. Data E3 shows the relation between the shift amount d and the signal intensity of the optical beat signal, in a case where the blood flow velocity is measured with a distance g of 2 mm between the upper surface of the sensor part of the blood flow sensor device in the comparative example and the measurement point Q1.

As shown in the data E1, E2, and E3, in the blood flow sensor device in the comparative example, the detected signal intensity of the optical beat signal rapidly decreases in accordance with an increase in the shift amount d. In other words, if the position relation between the fingertip 500 and the sensor part changes, there is a possibility that the blood flow velocity cannot be stably measured.

However, as shown in the data D1 and D2 in FIG. 14, in the blood flow sensor device in the first embodiment, the detected signal intensity of the optical beat signal hardly decreases even if the shift amount d increases, in comparison with the blood flow sensor device in the comparative example. In other words, the range of the shift amount d where the blood flow velocity can be measured is wider than in the blood flow sensor device in the comparative example. That is, as shown in the data E1, E2, and E3 in FIG. 15, the range of the shift amount d where the blood flow velocity can be measured is less than or equal to about 1 mm at the widest in the blood flow sensor device in the comparative example, whereas as shown in the data D1 in FIG. 14, the range of the shift amount d where the blood flow velocity can be measured is less than or equal to about 2 mm in the blood flow sensor device in the first embodiment. Moreover, as shown in the data D2 in FIG. 14, in the case where the distance g is 8 mm, i.e. in the case where the thickness of the scatterer 200 is 8 mm, even if the shift amount d is e.g. 5 mm, the reduction in the detected signal intensity of the optical beat signal is small, and thus the blood flow velocity can be measured well. As described above, in the blood flow sensor device in the first embodiment, it is possible to reduce the change in the signal intensity of the optical beat signal detected by the photodiode 160, which is caused by the shift in the relative position relation between the sensor part 100 and the fingertip 500 as the specimen, in comparison with the blood flow sensor device in the comparative example. In other words, in the blood flow sensor device in the first embodiment, the range of the shift amount d where the appropriate detection value can be obtained is wider (i.e. the acceptable range of the shift amount d allowed to obtain the appropriate detection value in the measurement is wider) than in the blood flow sensor device in the comparative example. Here, the blood flow sensor device in the first embodiment and the blood flow sensor device in the comparative example are different in whether or not the scatterer 200 is provided, and they are constructed in substantially the same manner in other points. In other words, the effect of reducing the change in the signal intensity of the optical beat signal, which is caused by the shift in the relative position relation between the sensor part and the specimen, can be obtained because the blood flow sensor device in the first embodiment is provided with the scatterer 200.

Therefore, according to the blood flow sensor device in the first embodiment, the sensor par 100 is provided with the scatterer 200, so that it is possible to stably detect the blood flow velocity of the fingertip 500 on the basis of the optical beat signal. As a result, it is possible to increase the reliability of the detection value detected by the blood flow sensor device.

Incidentally FIG. 14 shows the case where the towel fiber is used as the scatterer; however, the inventors in the present application obtain substantially the same measurement results even if a nonwoven fabric and a sponge are used as the scatterer.

Moreover, according to the blood flow sensor device in the first embodiment, the sensor part 100 is provided with the scatterer 200, so that it is also possible to limit or prevent that the detected signal intensity of the optical beat signal is reduced by applying a relatively large pressure to the specimen.

Figure 16:
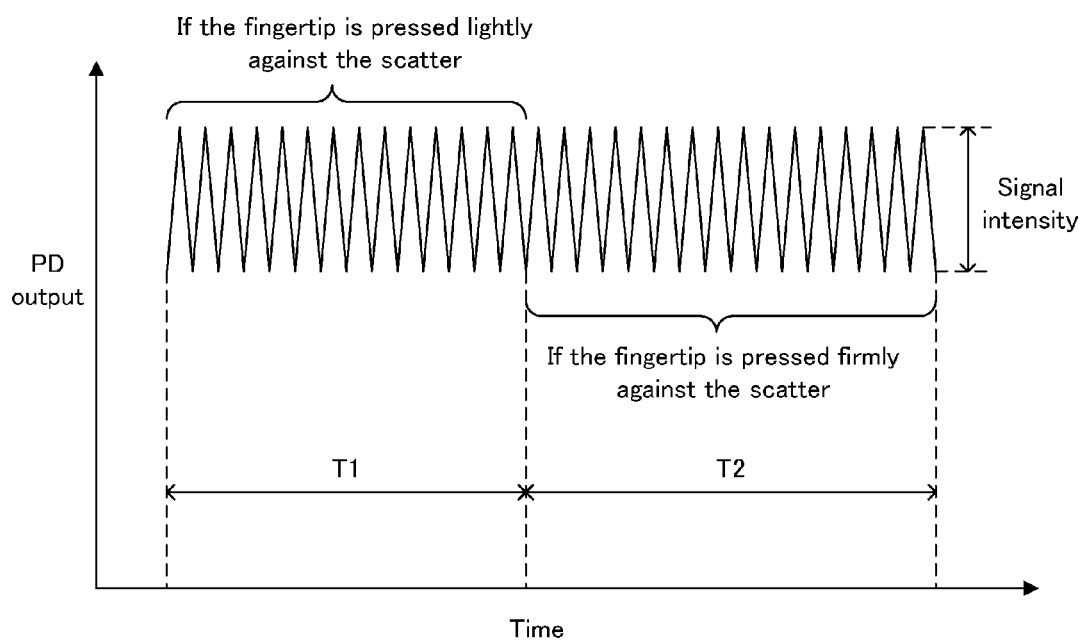
FIG. 16 is a graph showing the signal intensity of the optical beat signal detected by the blood flow sensor device in the first embodiment, by comparing a case where the specimen is pressed slightly against the scatterer with a case where the specimen is pressed firmly against the scatterer.
Figure 17:
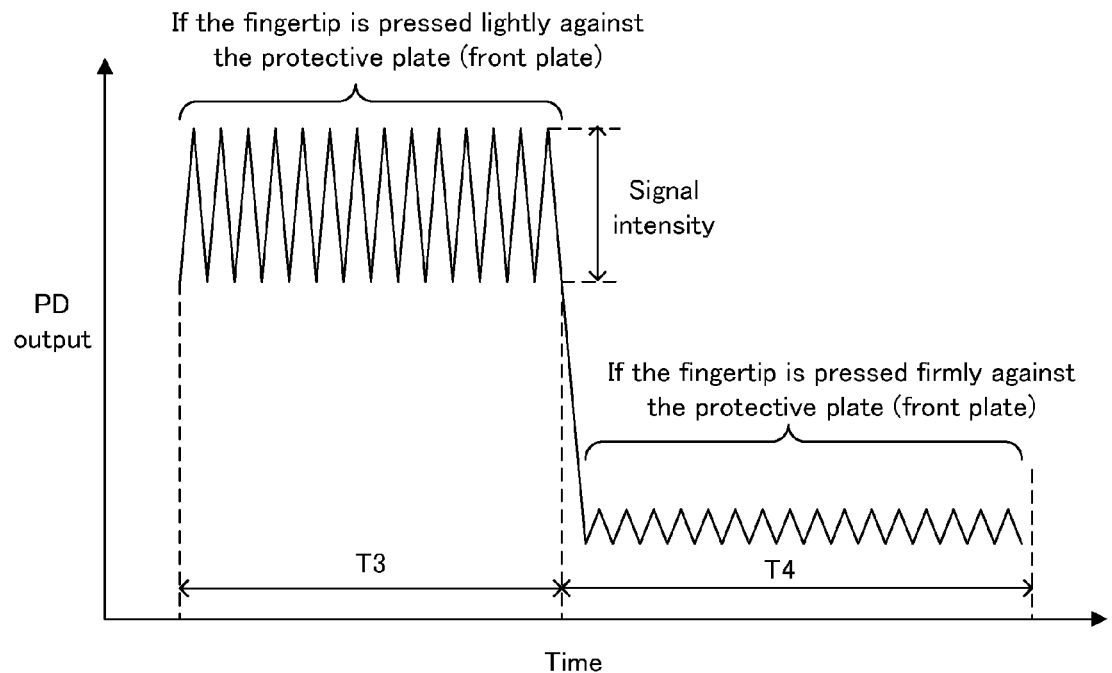
FIG. 17 is a graph showing the signal intensity of the optical beat signal detected by the blood flow sensor device in the comparative example, by comparing a case where the specimen is pressed slightly against the upper surface of the sensor part with a case where the specimen is pressed firmly against the upper surface of the sensor part.

FIG. 16 is a graph showing the signal intensity of the optical beat signal detected by the blood flow sensor device in the first embodiment, by comparing a case where the specimen is pressed slightly against the scatterer with a case where the specimen is pressed firmly against the scatterer. FIG. 17 is a graph showing the signal intensity of the optical beat signal detected by the blood flow sensor device in the comparative example, by comparing a case where the specimen is pressed slightly against the upper surface of the sensor part with a case where the specimen is pressed firmly against the upper surface of the sensor part. Incidentally, in FIG. 16 and FIG. 17, the horizontal axis indicates a time axis, and the vertical axis indicates the intensity of an output signal from the photodiode (PD output). The signal intensity of the optical beat signal means the amplitude of the optical beat signal.

FIG. 16 shows a change over time in the detected signal intensity of the optical beat signal in the case where the blood flow velocity is measured in the condition that the fingertip, which is one example of the specimen, is pressed lightly against the scatterer 200 in a period T1 and the blood flow velocity is measured in the condition that the fingertip, which is one example of the specimen, is pressed firmly against the scatterer 200 in a period T2 following the period T1, by using the blood flow sensor device in the first embodiment. Incidentally, in this measurement, the towel fiber is used as the scatterer 200.

As shown in FIG. 16, according to the blood flow sensor device in the first embodiment, the signal intensity of the optical beat signal rarely changes (i.e. almost the same) between the case where the fingertip is pressed lightly against the scatterer 200 and the case where the fingertip is pressed firmly against the scatterer 200.

On the other hand, FIG. 17 shows a change over time in the detected signal intensity of the optical beat signal in the case where the blood flow velocity is measured in the condition that the fingertip, which is one example of the specimen, is pressed lightly against the sensor part (more specifically, e.g. the upper surface of the protective plate made of a resin substrate, a glass substrate, or the like) in a period T3 and the blood flow velocity is measured in the condition that the fingertip, which is one example of the specimen, is pressed firmly against the sensor part in a period T4 following the period T3, by using the blood flow sensor device in the comparative example.

As shown in FIG. 17, according to the blood flow sensor device in the comparative example, the signal intensity of the optical beat signal decreases in the case where the fingertip is pressed firmly against the sensor part, in comparison with the case where the fingertip is pressed lightly against the sensor part. One of the causes of this phenomenon is that a relatively large pressure is applied on the fingertip by the fingertip being pressed firmly against the sensor part and thus the blood capillaries of the fingertip tend to be occluded or blocked.

However, the blood flow sensor device in the first embodiment is provided with the scatterer 200 made of the towel fiber in this measurement, so that it is possible to prevent that a relatively large pressure is applied to the fingertip, which is one example of the specimen, and it is also possible to limit or control that the blood capillaries of the fingertip tend to be occluded or blocked. Thus, as shown in FIG. 16, the signal intensity of the optical beat signal rarely changes between the case where the fingertip is pressed lightly against the scatterer 200 and the case where the fingertip is pressed firmly against the scatterer 200. Therefore, it is possible to reduce or prevent that the measured blood flow velocity changes depending on a change in power of the fingertip being pressed against the upper surface of the sensor part 100 (or the upper part of the scatterer 200 in the first embodiment). As a result, it is possible to stably measure the blood flow velocity. Incidentally, the effect that the blood flow velocity can be stably measured regardless of the change in power for the specimen being pressed against the sensor part can be obtained not only in the case where the scatterer 200 is made of the towel fiber but alto in a case where the scatterer 200 is made of another fibrous material or sponge or the like and is softer or has higher elasticity than the protective plate and the front plate.

As explained in detail above, according to the blood flow sensor device in the first embodiment, it is provided with the scatterer 200, so that the change in the detection value (i.e. the blood flow velocity) caused by the shift in the relative position relation between the blood flow sensor device and the specimen is reduced, and the blood flow velocity of the specimen can be stably detected. Moreover, it is possible to reduce that the measured blood flow velocity changes due to the change in power of the specimen being pressed against the upper surface of the sensor part.

The present invention is not limited to the aforementioned example, but various changes may be made, if desired, without departing from the essence or spirit of the invention which can be read from the claims and the entire specification. A light-emitting sensor device, which involves such changes, is also intended to be within the technical scope of the present invention.

INDUSTRIAL APPLICABILITY

The light-emitting sensor device of the present invention can be applied to a blood flow sensor device or the like capable of measuring a blood flow velocity or the like.

The invention claimed is:
1. A light-emitting sensor device comprising:
a substrate;
an irradiating part, disposed on said substrate, for applying light to a specimen;

a light receiving part, disposed on said substrate, for detecting light from the specimen caused by the applied light;

a light scattering part, adapted to be disposed at least one of between said irradiating part and the specimen and between the specimen and said light receiving part, for scattering at least one of light emitted from said irradiating part and the light from the specimen; and a front plate disposed to face said substrate, on a front surface side where the specimen is disposed with respect to said substrate, wherein said light scattering part is disposed to wrap around said front plate and has a higher elasticity than an elasticity of said front plate.

2. The light-emitting sensor device according to claim 1, wherein said light scattering part includes a fibrous material.

3. The light-emitting sensor device according to claim 1, wherein said light scattering part includes foam.

4. The light-emitting sensor device according to claim 1, wherein said light scattering part has a plurality of scattering materials dispersed in a transparent member which can transmit the at least one light, each of the plurality of scattering materials having a refractive index which is different from a refractive index of the transparent member, the plurality of scattering materials being capable of scattering the at least one light.

5. The light-emitting sensor device according to claim 1, wherein, said light scattering part is bonded to said front plate by an adhesive which can transmit the at least one light.

6. The light-emitting sensor device according to claim 1, further comprising a light shielding part, disposed between said irradiating part and said light receiving part on said substrate, for shielding between said irradiating part and said light receiving part from light.

7. The light-emitting sensor device according to claim 1, wherein said irradiating part and said light receiving part are integrated on said substrate.

8. The light-emitting sensor device according to claim 1, further comprising a calculating part for calculating a blood flow velocity associated with the specimen, on the basis of the detected light.

9. The light-emitting sensor device according to claim 1, wherein said irradiating part has a semiconductor laser for generating laser light as the light.

* * * * *

UNITED STATES PATENT AND TRADEMARK OFFICE
CERTIFICATE OF CORRECTION

PATENT NO. : 8,591,426 B2  Page 1 of 1
APPLICATION NO. : 12/991965
DATED : November 26, 2013
INVENTOR(S) : Onoe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 483 days.

Signed and Sealed this
Twenty-second Day of September, 2015

Michelle K. Lee
*Director of the United States Patent and Trademark Office*